United States Patent [19]

Motschan

[11] Patent Number: 4,619,829

[45] Date of Patent: Oct. 28, 1986

[54] UTILIZATION OF A SINGLE VITAMIN OR A COMBINATION OF VARIOUS VITAMINS

[76] Inventor: Georges Motschan, Schönbeinstrasse 21, 4056 Basel, Switzerland

[21] Appl. No.: 631,555

[22] PCT Filed: Nov. 16, 1983

[86] PCT No.: PCT/CH83/00127

§ 371 Date: Jul. 13, 1984

§ 102(e) Date: Jul. 13, 1984

[87] PCT Pub. No.: WO84/01899

PCT Pub. Date: May 24, 1984

[30] Foreign Application Priority Data

Nov. 16, 1982 [CH] Switzerland ............... 6682/82

[51] Int. Cl.$^4$ ............... A61K 31/525; A61K 33/42
[52] U.S. Cl. ............... 424/128; 514/251; 514/825; 514/904; 514/905
[58] Field of Search ............... 514/276, 251, 825, 904, 514/905; 424/128

[56] References Cited

U.S. PATENT DOCUMENTS

| | | | |
|---|---|---|---|
| 1,261,995 | 4/1918 | Ampt | 424/355 |
| 2,816,854 | 12/1957 | Gross | 424/143 |
| 4,206,222 | 6/1980 | Valetas | 424/279 |
| 4,386,072 | 5/1983 | Horrobin et al. | 424/127 |
| 4,387,093 | 6/1983 | Lysaght | 424/131 |
| 4,439,454 | 3/1984 | Riva | 424/329 |

OTHER PUBLICATIONS

Chem. Abst., 72, 99038q, (1970)—Guglielmi et al.
Chem. Abst., 74, 73981h, (1971)—Fukui.
Chem Abst., 76, 21283d, (1972)—Alter et al.
Chem. Abst., 76, 70679(w), (1972)—Kurmaeva et al.
Chem. Abst., 81, 131090z, (1974)—Nash.
Chem. Abst., 90, 70869x, (1979)—Miskinite et al.
Chem. Abst., 90, 145621w, (1979)—Wilkins et al.
"The Healing Factor"—Irwine Stone—1972—pp. 108–112.

Primary Examiner—Douglas W. Robinson
Attorney, Agent, or Firm—Ostrolenk, Faber, Gerb & Soffen

[57] ABSTRACT

The invention refers to a new utilization of a unique vitamin or a combination of various vitamins in the long-term treatment and/or prevention of rheumatic diseases.

During a long-term treatment and/or prevention of rheumatic diseases, a unique vitamin or a combination of various vitamins is administered to a patient.

9 Claims, No Drawings

UTILIZATION OF A SINGLE VITAMIN OR A COMBINATION OF VARIOUS VITAMINS

The present invention refers to a new utilization of a single or a combination of various vitamins in the long-term therapy and/or prophylaxis of rheumatic diseases and a method for a long-term therapy and/or prophylaxis of rheumatic diseases.

Rheumatic diseases are widespread illnesses. In the USA alone about 30 million people suffer from arthritis, vide TIME MAGAZINE nr. 33, page 41, of Aug. 16, 1982. In the "Bulletin on the Rheumatic Diseases", vol. 32, nr. 1 (1982), page 1, published by the Arthritis Foundation, 3400 Peachtree Road, N.E. Atlanta, Ga. 30326, well-known therapies of rheumatoid arthritis are described.

The active substances collectively denominated vitamins are known, vide for example "Chemie Lexikon" by Prof. Dr. Hermann Römpp, Franckh'sche Verlagshandlung, Stuttgart.

It is described in the literature that neither short-term administration of vitamins nor high-level doses and/or so-called massive doses result in improvement in cases of rheumatoid arthritis; vide "Arthritis and Allied Conditions. A Textbook of Rheumatology". Editor: Joseph Lee Hollander, M.D., Seventh Edition. Published (in Europe) by Henry Kimpton, London, 1966, especially chapter 37, "Diet and Vitamins in Rheumatoid Arthritis", by Ronald Lamont-Havers, M.D.

Completely surprisingly, it now was found that rheumatic diseases can very successfully be treated by administration of at least one vitamin over a long period of time, be it prophylactically, for improvement and/or recovering.

The present invention refers to a new application of a single or a combination of various vitamins in the long-term therapy and/or prophylaxis of rheumatic diseases, especially such of inflammatory and degenerative nature, which involve joints, muscles, tendines and other parts of the locomotive system. Examples of such diseases are the inflammations of joints, chronical polyarthritis, a primary chronical polyarthritis and a general arthritis, especially a chronical and/or acute arthritis. The word "Polyarthritis" has hereafter to be interpreted as a collective expression for all possible forms of appearances of this disease(s) and its aetiology(ies), be it rheumatoid arthritis, primary chronical polyarthritis, osteoarthritis or any of the more than 100 other forms and variations, symptoms and syndromes of this disease. Hereafter the supreme and collective expression polyarthritis will be used.

The long-term therapy can be applied in any way; the systemic, injection and the topical administrations are preferred. Above all, however, the most preferable is the oral administration. The active substances acting as antirheumatic agents are administered orally and/or by injection in a dosage of about 0.25–2 mg/kg body weight per day, preferably 0.5–1 mg/kg/per day, although higher or lower doses can be applied too and easily determined by an expert, for example a physician. In vitamin combinations, the quantities of the specific vitamins can be varied. The dose can be administered as a single-dose or be dispensed over several part-doses. For the preferred oral administration the customary modes are to be taken into consideration, such as capsules, lacquered tablets or tablets. The manufacture of such modes of administration can be the customary one.

It is of the utmost importance that an application in conformity with the invention is a long-term therapy, in conformity with the invention. The expression "long-term therapy" ordinarily depends on the degree of the disease to be treated, the general state of health of the patient, his body weight and his age. The expert will easily find out how long the treatment has to last until improvement or complete healing is achieved. If need be, the daily administration of the active substance or of the combination of active substances can be interrupted for a specific period of time, for instance 1 week or 1 month or longer and can subsequently be resumed at the same, an increased or a decreased rate. Depending on the specificity of the patient's individuality, it has been found, priority has to be given to a long-term therapy of not less than 5 months, especially not less than 6 months, preferably 1 year, and better still not less than 2 years. In some cases, it appears to be of the utmost advantage for the patient if the long-term treatment lasts for life.

Special preference is to be given to the long-term, regular, continuous, uninterrupted and daily application, in conformity with the invention, of an active substance or a combination of active substances in conformity with the invention, in order to achieve healing and/or stoppage and/or prevention (prophylaxis) of a rheumatic disease, especially of a polyarthritis in general and of a primary chronical polyarthritis.

Preferably the vitamin or vitamins belong to the vitamin-B-complex; regarding this term's definition the above mentioned "Chemie Lexikon" for example serves as reference.

The application of the vitamin or a combination of vitamins can be, in conformity with the invention, combined and supplemented with a mineral and/or trace element and/or at least an additive, especially carriers, antioxidants, bacteriostats.

Following hereunder the specific newly applicable compounds, in conformity with the invention, are described, their synonyms, their biological preliminary stages (if any) and their chemical denominations:

VITAMIN A

Synonyms:
Retinol
Axerophtol
Antixerophtalmic vitamin
Antiinfectuous vitamin
Skin protecting vitamin
Growth vitamin
  Biological preliminary stages:
α-,β-,γ-Carotin
Cryptoxanthin (3-Hydroxy-β-carotin)
Echineon (4-oxo-β-carotin)
Citroxanthin (Mutatochrome; β-carotinoxide)
Myxoxanthin
Torularhodin
Aphanin
  Chemical Denominations:

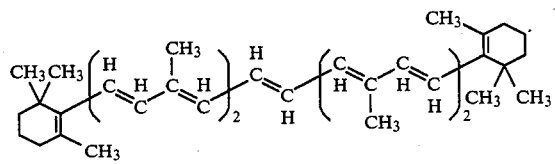

all-trans-β-carotin

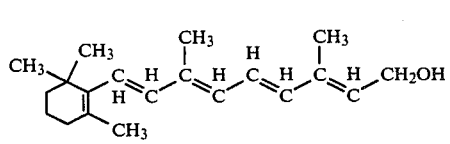

all-trans-vitamin A₁ = all-trans-3,7-dimethyl-9-(2',6',6'-trimethyl-1'-cyclohexen-1'-yl)-2,4,6,8-nonatetraen-1-ol

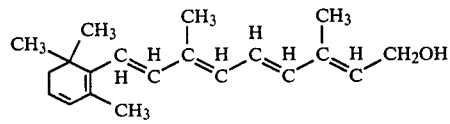

all-trans-vitamin A₂ = 3',4'-Dehydrovitamin A₁

VITAMIN B₁

Synonyms:
Thiamine
Aneurine
Antineuritic vitamin
Anti-Beriberi-vitamin
Beriberi Preventive Substance
Torulin
  Chemical Denomination

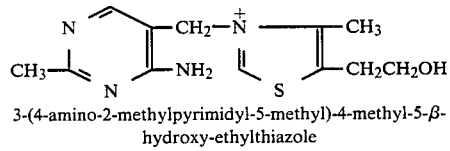

3-(4-amino-2-methylpyrimidyl-5-methyl)-4-methyl-5-β-hydroxy-ethylthiazole

VITAMIN B₂

Synonyms:
Riboflavin
Lactoflavin
  Chemical Denomination:

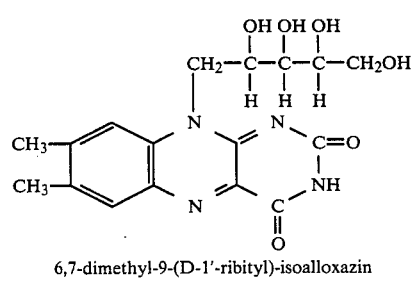

6,7-dimethyl-9-(D-1'-ribityl)-isoalloxazin

NICOTINAMIDE

Synonyms:
Nicotinamide
Nicotylamide
Niacinamide
Vitamin PP
Pellagra Preventive Factor
PP Factor
Pellagra preventive factor
  Chemical Denomination:

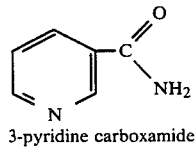

3-pyridine carboxamide

VITAMIN B₆

Synonyms:
Pyridoxine
Adermin
Anti-acrodynic-factor
Anti-dermatitis-factor
Rat Pellagra Preventive Factor
  Chemical Denominations:

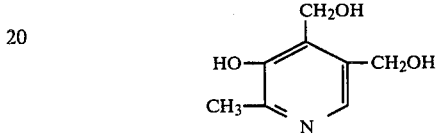

2-methyl-3-hydroxy-4,5-di(hydroxymethyl)-pyridine
Pyridoxole

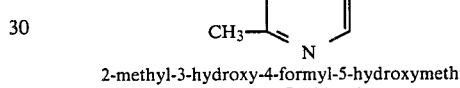

2-methyl-3-hydroxy-4-formyl-5-hydroxymethyl-pyridine
Pyridoxal

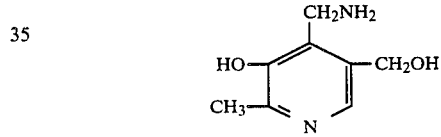

2-methyl-3-hydroxy-4-aminomethyl-5-hydroxymethyl-pyridine
Pyridoxamine

The group of the 3 active substances Pyridoxole, Pyridoxal, Pyridoxamine, all of which have vitamin-B₆ effects, are gathered under the denomination Pyridoxine.

PANTOTHENIC ACID

Synonyms:
Filtrate factor
Bios IIa
Bios III
Chick-anti-dermatitis-factor
Anti-gray (hair)-factor
  Chemical Denominations:

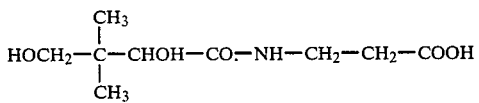

D(+)-αγ-dihydroxy-β, β-dimethylbutyryl-β'-alanin

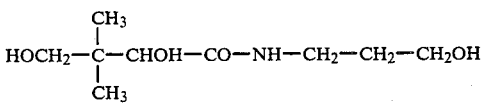

Pantothenyl alcohol (Panthenol)
Salts: Pantothenic calcium (Calcium-D-Pantothenate)

BIOTIN

Synonyms:
Vitamin H
Bios II
Bios IIb
Coenzyme R
Skin Factor
Antisebaceous vitamin
  Chemical Denomination:

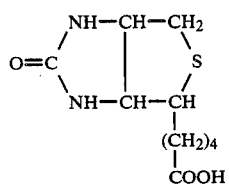

3,4-(2'-ketoimidazolido)-2(ω-carboxylbutyl)-thiophan(β-Biotin)

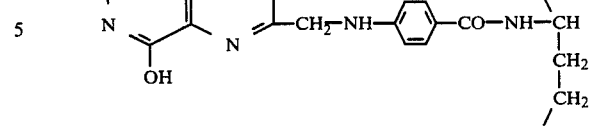

N—[4-([(2-amino-4-hydroxy-6-pteridyl)methyl]-amino)benzoyl]-glutamic acid

VITAMIN $B_{12}$

Synonyms:
Cyanocobalamin
Erythrocine
Animal protein factor (APF)
Antipernicious Anaemia Factor
Extrinsic Factor (CASTLE)

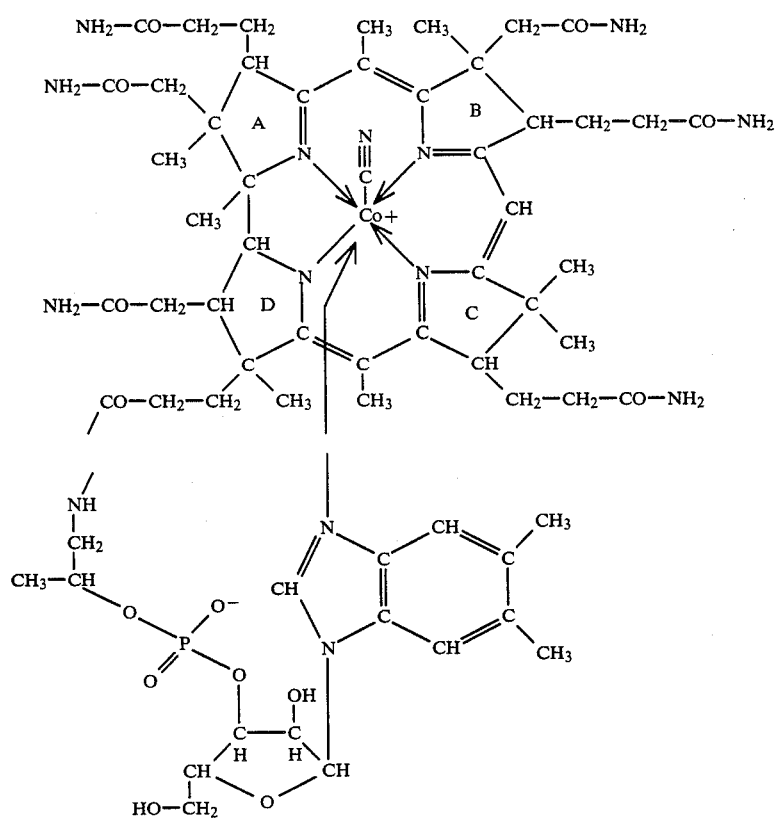

So far, a considerable number of vitamin-$B_{12}$-factors (Cobalamins) have been isolated and represented. They differ from each other by distinct nucleous parts and show different biological activities. Vitamin $B_{12}$ is extracted mainly from residues of cultures of *Streptomyces griseus* and similar organisms.

FOLIC ACID

Synonyms:
Pteroglutamic Acid
Vitamin $B_c$
Vitamin M
Eluate Factor (Liver)
Lactobacillus casei factor
Chemical Denomination:

VITAMIN C

Synonyms:
Ascorbic acid
Antiscorbutic acid
Antiscorbutic vitamin
Antiscorbutine
Hexuronic acid
  Chemical Denominations:

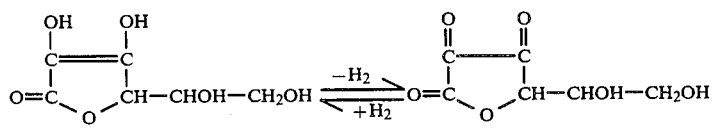

Ascorbic Acid = L—threo-2,3,4,5,6-pentoxy-hexon-2-carbonic-acid-lactone = L—threo-3-ketohexuronic-acid-enole-lactone Dehydroascorbic acid = 2,3-diketo-L—gulono-lactone

VITAMIN D

Synonyms:
Calciferol
Anti-Rachitis-Vitamin
Chemical Denominations:

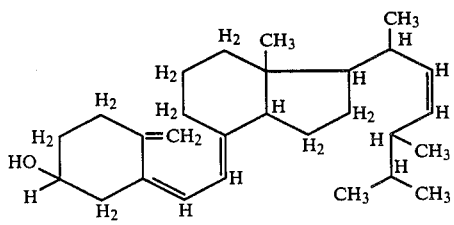

Vitamin $D_2$: Ergocalciferol
(Irradiated product of the ergosterols)

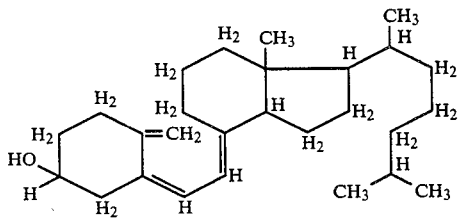

Vitamin $D_3$: Cholecalciferol
(Irradiated product of the 7,8-dehydro-cholesterol)

Apart from vitamins $D_2$ and $D_3$, which alone for themselves are applied therapeutically, a series of related compounds have been detected, all of which together with the former named vitamins comprise the so-called group of vitamin-D.

Vitamin $D_1$: Molecular compound of Vitamin $D_2$ and lumisterol$_2$ (irradiated product of ergosterol). Nonexistant in nature.

Vitamin $D_4$: Irradiation product of 22,23-dihydroergosterol;

Vitamin $D_5$: Irradiation product of 7-dehydrositosterol;

Vitamin $D_6$: Irradiation product of 7-dehydrostigmasterol;

Vitamin $D_7$: Irradiation product of 7-dehydrocamposterol (isomer to 22,23-dihydroergosterol).

VITAMIN E

Synonyms:
Tocopherol
Anti-dystrophy-vitamin
Anti-sterility-vitamin
Fertility-vitamin Vitamin E stands for the the whole group of Tocopherols, which differ from each other by number and position in the methyl groups on the hydroxychrome-ring, partly also by the presence of double compounds within the phytyl side chain. Generally however vitamin E is understood to be the α-Tocopherol or its acetate, which possesses the greatest efficacy amongst all tocopherols.

Chemical Denominations:

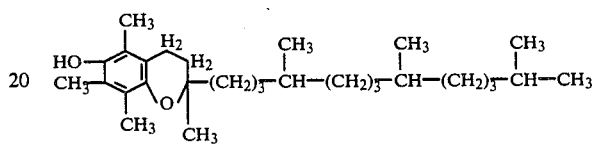

α-Tocopherol: 2,5,7,8-Tetramethyl-2-(4',8',12'-trimethyl-dodecyl)-chroman-6-ol or 5,7,8-trimethyl-tocol
β-Tocopherol: 5,8-dimethyltocol
γ-Tocopherol: 7,8-dimethyltocol
δ-Tocopherol: 8-Monomethyltocol
ε-Tocopherol: 2-Farnesyl-2,5,8-tetramethylchroman-6-ol
ζ-Tocopherol: 2-Farnesyl-2,5,7,8-tetramethylchroman-6-ol
η-Tocopherol: 2-Monomethyltocol Hereunder are some exemplary preferred combinations of active substances for the application in conformity with the invention and the method in conformity with the invention are represented, emphasizing that the present invention is not restricted to such combinations only. Their manufacture to be the usual one.

1. Vitamin-B-complex factors.
Composition
Active Substances: the main factors of the vitamin-B-complex in pure form and in therapeutically adjusted relations to quantities.

| Types: | Drops per ml (20 drops) | Tablets "forte" per tablet *) | Sirup per 5 ml | Ampoules per ampoule (2 ml) |
|---|---|---|---|---|
| Vitamin $B_1$ | 5 mg | 15 mg | 5 mg | 10 mg |
| Vitamin $B_2$ | 2 mg | 15 mg | 2 mg | 4 mg |
| Nicotinamide | 20 mg | 50 mg | 20 mg | 40 mg |
| Vitamin $B_6$ | 2 mg | 10 mg | 2 mg | 4 mg |
| Calciumpantothenate | — | 25 mg | — | — |
| Panthenol | 3 mg | — | 3 mg | 6 mg |
| Biotin | 0.25 mg | 0.15 mg | — | 0.5 mg |
| Vitamin $B_{12}$ | 4 μg | 10 μg | — | 8 μg |

1 ml drops contain 1.14 g carbohydrates, corresponding to 4.7 kilo calories. 1 tablet (forte) 270 mg, corresp. to 1.1 kilo calories, and 5 ml sirup 4.02 g, corresponding to 16.5 kilo calories.
(*) this composition is denominated hereunder as "Combination I".

2. Vitamin-B-Complex together with Vitamin C (tablets, resp. with Vitamin C and Calcium (effervescent tablets).
Composition

| | Per tablet (**) | Per effervescent tablet |
|---|---|---|
| Vitamin $B_1$ | 15 mg | 15 mg |
| Vitamin $B_2$ | 15 mg | 15 mg |
| Nicotinamide (PP-factor) | 50 mg | 50 mg |

2. Vitamin-B-Complex together with Vitamin C (tablets, resp. with Vitamin C and Calcium (effervescent tablets).
Composition

| | Per tablet (**) | Per effervescent tablet |
|---|---|---|
| Vitamin $B_6$ | 10 mg | 10 mg |
| Calciumpantothenate | 25 mg | 25 mg |
| Biotin | 0.15 mg | 0.15 mg |
| Vitamin $B_{12}$ | 10 $\mu$g | 10 $\mu$g |
| Vitamin C | 500 mg | 1000 mg |
| Calcium carbonate | — | 156.25 mg |
| Calcium glycerophosphate | — | 327 mg |

1 Effervescent tablet contains 704 mg carbohydrates, corresponding to 2.9 kilo calories; each effervescent tablet contains besides about 230 mg Na (corr. to abt. 0.6 g NaCl). When strict low-salt regimen is applied the adminstration of tablets insteadof effervescent tablets is advisable.
(**) This composition is denominated "Combination II" hereunder.

| 12 Vitamins | Polyvitamin Preparation Combination | | |
|---|---|---|---|
| | Per effervescent tablet | Per tablet | Per capsule (***) |
| Vitamin A | 25 000 I.U. | 25 000 I.U. | 25 000 I.U. |
| Vitamin $B_1$ | 20 mg | 20 mg | 20 mg |
| Vitamin $B_2$ | 5 mg | 5 mg | 5 mg |
| Nicotinamide | 50 mg | 50 mg | 50 mg |
| Vitamin $B_6$ | 10 | 10 mg | 10 mg |
| Panthenol | — | — | 10 mg |
| Calcium pantothenate | 11.6 mg | 11.6 mg | — |
| Biotin (Vitamin H) | 0.25 mg | 0.25 mg | 0.25 mg |
| Vitamin $B_{12}$ | 5 $\mu$g | 5 $\mu$g | 5 $\mu$g |
| Folic acid | 1 mg | 1 mg | 1 mg |
| Vitamin C | 150 mg | 150 mg | 150 mg |
| Vitamin D | 500 I.U. | 500 I.U. | 1000 I.U. |
| Vitamin E | 10 mg | 10 mg | 10 mg |

| 8 Minerals and trace elements | Per effervescent tablet | Per tablet | Per capsule |
|---|---|---|---|
| Calcium | 262 mg $CaC_3H_5(OH)_2PO_4$ | 129 mg $Ca_3(PO_4)_2$ | 435 mg $CaHPO_4.2H_2O$ |
| Iron | 12.5 mg Fe carbonic. sacc. | 50 mg $FeSO_4.7H_2O$ | 10 mg Fe reduct. |
| Magnesium | 40 mg $MgC_3H_5(OH)_2PO_4$ | 30 mg MgO | 36.5 mg $MgHPO_4.3H_2O$ |
| Mangan | 2.05 mg $MnSO_4.4H_2O$ | 2.05 mg $MnSO_4.4H_2O$ | 2.05 mg $MnSo_4.4H_2O$ |
| Copper | 0.39 mg $CuSO_4.5H_2O$ | 3.9 mg $CuSO_4.5H_2O$ | 3.9 mg $CuSO_4.5H_2O$ |
| Zinc | 2.3 mg $ZnSO_4.7H_2O$ | 2.3 mg $ZnSO_4.7H_2O$ | 2.3 mg $ZnSO_4.7H_2O$ |
| Molybdenum | 0.25 mg $Na_2MoO_4.2H_2O$ | 0.25 mg $Na_2MoO_4.2H_2O$ | 0.25 mg $Na_2MoO_4.2H_2O$ |
| Phosphorus | 45 mg sub forma $PO_4$ | 79 mg sub forma $PO_4$ | 83.9 mg sub forma $PO_4$ |

1 effervescent tablet contains 891 mg carbo hydrates, corresponding to 3,6 kilo calories; moreover 300 mg Na (corr. abt. 0.7 g NaCl); 1 tablet 350 mg, corr. 1.4 kilo calories. Consequently patients observing low-salt regimen should be administered capsules or tablets instead of effervescent tablets.
***this combination is hereunder denominated as "Combination III".

The method in conformity with the invention for the long-term treatment and/or prophylaxis of rheumatic diseases is characterized by the administration to the patient of a single vitamin or a combination of various vitamins in variable quantities.

The method of application in conformity with the invention consists in the oral and/or per iniectio administration of the preferred above mentioned active substances.

The new application in conformity with the invention as well as the method in conformity with the invention are applied in both, human and veterinary medicines; for example in human beings and warm blooded animals, such as horses, cattle, cows, dogs, cats asf.

Hereunder, two cases are described:

CASE A

Female A was born Sept. 30, 1890, in St. Petersburg (today Leningrad), Russia, of Russian-Finnish descent, lives since 1924 in Zürich (Switzerland). Little is known about her parents, brothers and sisters, as no contact with them exists since 1934. Person A does not remember any more in 1982 what kind of illnesses had occurred in her faimily.

Person A enjoyed very good health until very old age. In 1964 at the age of 74 she overcame an appendectomy so striking lightly that the chief surgeon not only released her from hospital only one week after the operation, but allowed her expressively to immediately depart for holidays. At the outset of 1982, person A still had all her own teeth.

Person A measures about 153 cm and is finely shaped. A non-smoker throughout her life, she was always a "good eater", carnivorous, drinking little alcohol,—an occasional glass of wine and during meals only. Her weight in 1972 was was guessed to be about 47 kilos. It must have been in 1972, ten years ago, when she started to complain about "rheumatic pains" in her right shoulder and her right knee. Since 1948 widowed, she was very keen to walk daily about town, covering thus some 10 to 12 kilometers per day. Attacks of pain in the right knee automatically curtailed the extensions of such daily walks. The disease manifested itself slowly and insidiously only over years.

For a longer period of time—propably from 1973 through 1975—see consulted her house-doctor. Subsequently person A took in, on perscription of her physician, various NSAID-antirheumatics, such as Aspirin, Irgapyrin, Butazolidin, Volaterene and many others. No positive results were noted. When the physician started, in about 1975, to inject a substantial number of shots (exact figure not shown) directly into the knee (some gold-preparation), person A, then still a resolute person, decided to reject such painful therapy,—it is unknown after how long a time and after how many shots—and resolved to discontinue treatment of the polyarthritis altogether, preferring to live henceforth in pain from her "rheumatism" or to die of same. For person A such a resolution was a major one, for she had always expressed a significant determination for a long life of not less than 100 years.

Her polyarthritis developed only slowly, but progressively, as stated above, a fact easily to be noted because person A was checked in regular intervals (once a week).

Since about 1976 the patient had attacks of debility, which at the beginning were simply attributed to old age and considered to be independent of polyarthritis.

Only when she started to complain more specifically about stiff fingers in the mornings too, polyarthritis was taken into consideration. "Morning stiffness in the fingers" prevented her from getting dressed immediately after wake-up, to wash and prepare her breakfast. Person A lives by herself in a one-room apartment,—looking herself after her little household. She stated that she had to loosen her fingers by exercising for at least half an hour or a full hour. Moreover she distinctly tended to get tired quickly and to feel pain in the wrists, the front phalangeal joints (except the thumbs!); the skin on the phalanges in pain (front) swell tightly and turned reddish-violet and became inflamed and tense, all of which was so painful that person A was not to be touched at her hands.

The fingernails, those on the thumbs included, became brittle and somehow squamous, started to loosen themselves from their matrixes and tool unusual forms. Especially the two thumb-nails tended to ascend. Immediately next to the left wrist, at the level of the uppermost thumb-phalanx, a big and very painful swelling appeared, not very hard. Patient never admitted any fever. She never was persuaded to actually measure her temperature.

The right shoulder and the right knee pained doubtlessly so much that she started, for instance, to each using her left hand, obviously to avoid to move her right shoulder. Despite this development, going back to years, the old lady remained stubborn: she steadfastly refused to take any medicaments, even "light" analgesics.

In such circumstancrs the only thing left was to persuade her to at least take some tonic—a Geriatric Agent for instance—to fight off more frequent attacks of debility and great fatigue. To this she agreed and the aforementioned "Combination III" was prescribed. Ever since about 1976/1977 person A takes daily, regularly and uninterruptedly one capsule of "Combination III".

Shortly after staring the intake of "Combination III", the first positive reactions were to be noted insofar as attacks of debility began to disappear, slowly but clearly. Arthritic pains however persisted, fluctuating from sharp to untolerable, depending on weather conditions and other dispositions; consequently pains did not reduce, complaints about mobility of hands, fingers, right knee and right shoulder persisted immutably, only the general state of health of the patient, as far as one may speak of same in the patient's condition, seemed to turn to the better, despite of the advancing old age. Person A remained adamantly negative as regards all attempts to convince her to agree to the intake of some medicament against her "rheumatic" pains.

After many months of intake of the "Combination III" (the patient must have been taking the "Combination III" for at least 8–12 months), person A started to make remarks about her feeling better, how knee and shoulder were no more continuously in pain and that hands and fingers ached less. One could observe how some of the afore-described symptoms started to disappear, most strinkingly with the finger-nails, the front-phalanges: the inflammation of the fingers receded gradually. Person A stated that the morning-stiffness of the fingers, which disturbed her so much, prevailed for a shorter. Formerly such stiffness lasted for periods up to two hours; now after one half hour only the stiffness was gone. Her finger-nails began to look more or less "healthy". Only the two thumb-nails, most afflicted, still in November 1982 showed clear signs of traces of alterations, which however are also subsiding.

The hands of the patient A, years ago and for years highly sensitive due to pain- and pressure-sensitivity, are typical geriatric hands, completely free however of polyarthritic symptoms: One can today pump them unhestitatingly with no pain felt by the patient.

Occasional pains in the right shoulder and the right knee (person A blames same on an imminent change of weather) are supposedly only signs of attrition, as almost not inflamed any more.

A remarkable fact is to be seen insofar as person A has, since she seems to have overcome her polyarthritis thanks to "Combination III", gained weight in 1981 despite her old age, lightly though but noticeably in the light of an ever decreasing quantity of food-intake,—she gained about $2\frac{1}{2}$ to 3 kg.

CASE B

Male person B was born May 24, 1920 in Atkarsk (on the Volga river) in the USSR, in the midst of a famine. The family of person B was expelled 1924 from the USSR as undesired aliens (Swiss). Ever since, person B lives in Switzerland.

Father of person B died at the age of 59 (1948) of lung cancer. Both elder sisters of person B died at the ages of 45 and 58, both of carzinoma of the breast.

Polyarthritic diseases did not occur with either father or sisters of person B. Mother of person B manifested polyarthritic symptoms at an advanced age only. First symptoms directing to polyarthritis appeared in the case of person B about 9 years ago, i.e. in 1973: a singular, semi-hard and painful swelling on the middle joint of the right index of great obstinacy (it still exists today to a diminished extent but free from pain, thanks to a therapy with "Combination II"). No great attention was paid to this appearance. About 3 years ago, in 1979, it became observable that person B started to wake up in the mornings with finger-stiffness. After several months all front phalangeal joints (with the exception of the thumbs) showed red, painful swellings, which were tightly filled and which in the beginning of 1982 became so unpleasant and handicapping for person B that he had to fear to lose the faculty to write by hand or to type on the typewriter. The front phalanges became thick swollen and in the finger-tips there was a formicationtingling. The hands became so sensitive and pained so much that person B avoided whenever possible to shake hands with people. Person B suffered so much from pains in hands and fingers, that he resolved to take resolute measures: person B started to take "Combination III".

The first 30 capsules of "Combination III" did not bring the effect hoped for, on the contrary, an additional peculiar idiosyncrasy developed against the product: particular parts of the face started to "bloom", turned unhealthy-red, patchy, forcing to remove "Combination III" with the result that the allergy disappeared promptly. "Combination I" and "Combination II" were taken alternating. In June 1975, person B fractured his little right finger, requiring an operation. After the "screw" had been removed, the afflicted joint was slightly sensitive for some time. About 3 years later, only the operated-on finger-joint first started to show signs of inflammation and hardening. This inflammation of the finger-joint was of traumatic origin but persisted so long until the other 7 fingers showed similar inflammation- and pain-symptoms.

To fight off these unpleasant appearances "Combination I"/"Combination II" were employed (one tablet daily; effervescent tablets were avoided for their contents of calcium, because person B had had his bout with kidney-stones!) and it could be observed how, after about 8-12 months, first of all the front joint of the traumatised little finger healed so well that the remaining knot on the joint was completely free from pain even when strong pressure was applied.

After another 8-10 months, the inflammation of the joints as well as the inflammatory appearances on the 8 finger-joints (front) disappeared. There only must be added that, once one stops for some time the intake of "Combination I"/"Combination II" (for about 10-14 days), thereupon the joints of the 7 fingers, on which the idiopathic inflammatory process took place, start to pain, not acute yet, not violently, whereas the traumatised little right finger does not react to the stoppage.

Such tests of stoppage, tried several times, always had to be abandoned after 10-14 days, in order not to run the risk to call for renewed inflammations and pains.

In earlier years, person B often suffered from polyarthritic the pains in his left shoulder and left ankle, pains lasting not very long and which called for no special attention. It is however noteworthy that those sporadic occurring polyarthritic pains have completely disappeared, as a side-effect so to speak, just that person B still lives with a probably ossified swelling on the metatarsal bone, which does not hurt any more and is free from pain.

In connection with the disappearance of polyarthritis in the fingers of person B, another phenomenon has been observed: on some front finger-joints distinct knots remained. Today they are completely free from pain as long as the intake of "Combination I"/"Combination II" continues,—these distinct knots are receding ever so slowly. It is impossible to prove this phenomenon, as no X-rays exist which would allow comparisons. The above mentioned singular swelling on the middle joint of the right index has receded pointedly, only after considerable time, i.e. only months after intake of "Combination I"/"Combination II".

Besides: Person B is non-smoker since 20 years and takes nothing but "Combination I/"Combination II" and occasionally only if need be a medicament against headaches (Tonopan) and feels, after having overcome a polyarthritis, which was in the offing, completely in good health.

The life of person B went through two health-events: In 1949 he suffered from tuberculosis (closed), evidenced by photofluorography, which was completely cured; in 1968 person B fell victim to a serious car-accident, the consequences of which were a complicated fracture of the left arm. Those fractures were artfully repaired by osterosynthesis (2 titanium-plates with 13 screws): Person B is 1982 still wearing those two plates on his bones inclusive of the 13 screws without feeling no botheration at all.

As may be gathered from these two cases, the long-term application of for instance "Combination I", "Combination II" and "Combination III", can transform a manifest polyarthritis into a latent state of complaintlessness and painlessness, whereas the so-called "massive-doses" during the first months of therapy do not produce either positive or negative effects. Short-term and middle-term applications of preparations belonging to this group do not call for positive results as regards polyarthritis.

For these reasons it is important to especially emphasize that therapy (and prophylaxis) with the aforementioned preparations and the whole group of such preparations has to be on *long-term* over months.

The following table shows further data with respect to the aforementioned persons A and B:

TABLE

Therapy: of the rheumatism (of the primary chronicle polyarthritis)
Period of therapy: between 18 and 60 months

| Patient's sex and age | Daily dosage sec caption | Number of inv. joints | Strength of grip | Morning stiffness | Subjective feeling | Functional status | Fatigue | Pains | Sclerodermic symptoms | Side effects |
|---|---|---|---|---|---|---|---|---|---|---|
| Peron A, female, 92 years of age | months | | | | | | | | | |
| | 1 | 20 | 0 | 0 | 0 | 0 | 0 | 0 | 0 | none |
| | 3 | 20 | 0 | 0 | 0 | 0 | 0 | 0 | 0 | none |
| | 6 | 20 | 1 | 2 | 2 | 2 | 0 | 0 | 1 | none |
| | 9 | 12 | 2 | 3 | 2 | 1 | 1 | 1 | 1 | none |
| | 12 | 8 | 3 | 3 | 3 | 2 | 2 | 2 | 1 | none |
| | 18 | 2 | 4 | 4 | 4 | 3 | 2 | 3 | 4 | none |
| | 24 | 3 | 4 | 4 | 4 | 3 | 3 | 3 | 4 | none |
| | 30 | 3 | 4 | 4 | 4 | 3 | 2 | 3 | 4 | none |
| | 36 | 2 | 4 | 4 | 4 | 4 | 2 | 4 | 4 | none |
| | 42 | 2 | 4 | 4 | 4 | 4 | 3 | 4 | 4 | none |
| | 48 | 2 | 4 | 4 | 4 | 4 | 3 | 4 | 4 | none |
| | 54 | 2 | 4 | 4 | 4 | 4 | 4 | 4 | 4 | none |
| | 60 | 2 | 4 | 4 | 4 | 4 | 4 | 4 | 4 | none |
| Person B, male, 62 y. old | months | | | | | | | | | |
| | 1 | 9 | 0 | 0 | 0 | 0 | — | 0 | — | none |
| | 3 | 9 | 0 | 0 | 0 | 0 | — | 0 | — | none |
| | 6 | 6 | 2 | 2 | 3 | 3 | — | 2 | — | none |
| | 9 | 2 | 3 | 3 | 4 | 4 | — | 3 | — | none |
| | 12 | 0 | 4 | 4 | 4 | 4 | — | 4 | — | none |

TABLE-continued

| | | | Therapy: of the rheumatism (of the primary chronicle polyarthritis) Period of therapy: between 18 and 60 months | | | | | | | |
|---|---|---|---|---|---|---|---|---|---|---|
| Patient's sex and age | Daily dosage sec caption | Number of inv. joints | Strength of grip | Morning stiffness | Subjective feeling | Functional status | Fatigue | Pains | Sclerodermic symptoms | Side effects |
| | 18 | 0 | 4 | 4 | 4 | 4 | — | 4 | — | none |

Caption of table
The following marks have been applied in order to characterize results of therapy:
0 = no improvement
1 = slight improvement
2 = satisfactory improvement
3 = excellent improvement
4 = free from symptoms
— = no occurance of relevant symptoms The female person took in daily one capsule containing "Combination III".

The male person took in daily alternating one lacquered tablet, containing "Combination I", or one tablet containing "Combination II".

I claim:

1. A method for the treatment of polyarthritis which comprises the administration for a period of time of at least 5 months of an anti-arthritic effective amount of a vitamin composition comprising the combination of (a) about 0.15 to 0.5 mg of biotin, (b) about 5 to 20 mg of vitamin $B_1$, (c) about 2 to 15 mg of vitamin $B_2$, (d) about 20 to 50 mg of nicotinamide, (e) about 2 to 10 mg of vitamin $B_6$, (f) about 4 to 10 ug of vitamin $B_{12}$ and about 3 to 25 mg of pantothenic acid or the alcohol or calcium salt thereof.

2. The method of claim 1 in which the administration is for at least six months.

3. The method of claim 2 in which the administration is for at least one year.

4. The method of claim 3 in which the administration is at least two years.

5. The method of claim 1 in which the vitamin composition additionally contains a mineral.

6. The method of claim 1 in which the vitamin composition additionally contains a pharmaceutically acceptable carrier.

7. The method of claim 1 in which the vitamin composition administered comprises
15 mg Vitamin $B_1$
15 mg Vitamin $B_2$
50 mg Nicotinamide
10 mg Vitamin $B_6$
25 mg Calcium pantothenate
0.15 mg Biotin, and
10 ug Vitamin $B_{12}$.

8. The method of claim 1 in which the vitamin composition administered comprises
15 mg Vitamin $B_1$
15 mg Vitamin $B_2$
50 mg Nicotinamide (PP-Factor)
10 mg Vitamin $B_6$
25 mg Calcium pantothenate
0.15 mg Biotin
10 ug Vitamin $B_{12}$, and
500 mg Vitamin C.

9. The method of claim 1 in which the vitamin composition administered comprises
25,000 I.U. Vitamin A
20 mg Vitamin $B_1$
5 mg Vitamin $B_2$
50 mg Nicotinamide
10 mg Vitamin $B_6$
10 mg Panthenol
0.25 mg Biotin (Vitamin H)
5 ug Vitamin $B_{12}$
1 mg Folic Acid
150 mg Vitamin C
1,000 I.U. Vitamin D
10 mg Vitamin E,
435 mg $CaHPO_4.3H_2O$
10 mg Fe reduct,
36.5 mg $MgHPO_4.3H_2O$
2.05 mg $MnSO_4.4H_2O$
3.9 mg $CuSO_4.5H_2O$
2.3 mg $ZnSO_4.7H_2O$
0.25 mg $Na_2MoO_4.2H_2O$, and
83.9 mg Phosphorus sub form a $PO_4$.

* * * * *